US011547281B2

(12) United States Patent  
Yao et al.

(10) Patent No.: US 11,547,281 B2  
(45) Date of Patent: Jan. 10, 2023

(54) SHEATH ASSEMBLY FOR A RIGID ENDOSCOPE

(71) Applicant: Covidien LP, Mansfield, MA (US)

(72) Inventors: Hongwen Yao, Shanghai (CN); Zhentao Lu, Shanghai (CN); Zhenhai Zhang, Shanghai (CN); Yong Guo, Shanghai (CN)

(73) Assignee: Covidien LP, Mansfield, MA (US)

( * ) Notice: Subject to any disclaimer, the term of this patent is extended or adjusted under 35 U.S.C. 154(b) by 68 days.

(21) Appl. No.: 16/970,574

(22) PCT Filed: Feb. 15, 2018

(86) PCT No.: PCT/CN2018/076912  
§ 371 (c)(1),  
(2) Date: Aug. 17, 2020

(87) PCT Pub. No.: WO2019/157763  
PCT Pub. Date: Aug. 22, 2019

(65) Prior Publication Data  
US 2021/0113069 A1    Apr. 22, 2021

(51) Int. Cl.  
*A61B 1/00* (2006.01)
(52) U.S. Cl.  
CPC ...... *A61B 1/00135* (2013.01); *A61B 1/00096* (2013.01); *A61B 1/00114* (2013.01); *A61B 1/00128* (2013.01)
(58) Field of Classification Search  
CPC ............ A61B 1/00128; A61B 1/00135; A61B 1/00142; A61B 1/00154; A61B 46/10;  
(Continued)

(56) References Cited

U.S. PATENT DOCUMENTS 4,522,196 A * 6/1985 Cunningham ..... A61B 1/00142  
359/511  
4,550,715 A * 11/1985 Santangelo ............ A61B 17/34  
600/114  
(Continued)

FOREIGN PATENT DOCUMENTS

CN    105231979 A    1/2016  
CN    205339020 U    6/2016  
(Continued)

OTHER PUBLICATIONS

International Search Report dated Oct. 31, 2018 and Written Opinion completed Oct. 16, 2018 corresponding to counterpart Int'l Patent Application PCT/CN2018/076912.  
(Continued)

*Primary Examiner* — Michael J Carey  
*Assistant Examiner* — Stephen Floyd London  
(74) *Attorney, Agent, or Firm* — Carter, DeLuca & Farrell LLP

(57) ABSTRACT

A sheath for covering an endoscope includes a latch assembly, an elongate body extending distally from the latch assembly, and a sheath tip extending distally from the elongate body. The latch assembly includes a main housing and a guide housing, the guide housing movable relative to the main housing to increase a longitudinal length of the latch assembly. The sheath tip has a front face including first and second windows disposed within respective first and second openings defined in the front face. The first and second windows are configured to correspond with respective lighting and imaging windows of an endoscope.

19 Claims, 7 Drawing Sheets

(58) Field of Classification Search
CPC ...... A61B 2017/347; A61B 2050/0082; A61B 2050/0084; A61B 2017/00991; A61B 2017/3443
USPC .......................................................... 600/137
See application file for complete search history.

(56) References Cited

U.S. PATENT DOCUMENTS

| | | | | |
|---|---|---|---|---|
| 4,610,242 | A * | 9/1986 | Santangelo | A61B 17/34 600/114 |
| 4,914,521 | A * | 4/1990 | Adair | A61B 1/00142 348/375 |
| 5,301,657 | A * | 4/1994 | Lafferty | A61B 1/00096 206/438 |
| 5,311,358 | A * | 5/1994 | Pederson | A61B 46/10 359/510 |
| 5,609,564 | A * | 3/1997 | Makita | A61B 1/00142 374/158 |
| 5,704,892 | A | 1/1998 | Adair | |
| 5,741,084 | A * | 4/1998 | Del Rio | A61B 17/1633 285/361 |
| 5,876,328 | A * | 3/1999 | Fox | A61B 46/10 600/122 |
| 6,375,610 | B2 * | 4/2002 | Verschuur | A61B 46/10 600/122 |
| 6,695,772 | B1 * | 2/2004 | Bon | A61B 17/3421 600/114 |
| 7,954,397 | B2 | 6/2011 | Choi et al. | |
| 10,022,040 | B2 | 7/2018 | Cheng et al. | |
| 2006/0199998 | A1 | 9/2006 | Akui et al. | |
| 2006/0226655 | A1 * | 10/2006 | Smith | A61B 1/00154 285/401 |
| 2008/0064925 | A1 | 3/2008 | Gill et al. | |
| 2010/0286712 | A1 | 11/2010 | Won et al. | |
| 2010/0318101 | A1 | 12/2010 | Choi | |
| 2011/0015650 | A1 | 1/2011 | Choi et al. | |
| 2011/0022060 | A1 | 1/2011 | Won et al. | |
| 2011/0022229 | A1 | 1/2011 | Jang et al. | |
| 2011/0041160 | A1 | 2/2011 | Choi | |
| 2011/0261353 | A1 | 10/2011 | Teramura | |
| 2011/0277775 | A1 | 11/2011 | Holop et al. | |
| 2011/0292195 | A1 * | 12/2011 | Dahmen | A61B 1/00183 348/68 |
| 2012/0101508 | A1 | 4/2012 | Wook Choi et al. | |
| 2012/0289774 | A1 * | 11/2012 | Oskin | A61B 1/303 600/104 |
| 2013/0110129 | A1 | 5/2013 | Reid et al. | |
| 2014/0371763 | A1 | 12/2014 | Poll et al. | |

FOREIGN PATENT DOCUMENTS

| | | |
|---|---|---|
| DE | 102008059633 A1 | 6/2010 |
| WO | 2009104853 A1 | 8/2009 |
| WO | 2010008126 A1 | 1/2010 |
| WO | 2010068005 A2 | 6/2010 |
| WO | 2010123231 A2 | 10/2010 |
| WO | 2011021788 A2 | 2/2011 |
| WO | 2011037394 A2 | 3/2011 |
| WO | 2011052939 A2 | 5/2011 |
| WO | 2011115387 A2 | 9/2011 |
| WO | 2011149260 A2 | 12/2011 |
| WO | 2013018985 A1 | 2/2013 |

OTHER PUBLICATIONS

Extended European Search Report dated Aug. 27, 2021 corresponding to counterpart Patent Application EP 18906495.9.

* cited by examiner

SHEATH ASSEMBLY FOR A RIGID ENDOSCOPE

CROSS-REFERENCE TO RELATED APPLICATIONS

This application is a U.S. National Stage Application filed under 35 U.S.C. § 371(a) which claims the benefit of and priority to International Patent Application Ser. No. PCT/CN2018/076912, filed Feb. 15, 2018, the entire disclosure of which is incorporated by reference herein.

BACKGROUND

1. Technical Field

The present disclosure relates to medical devices and, more particularly, to sheath assemblies, and components thereof, for use with endoscopes.

2. Background of Related Art

Endoscopes are introduced through an incision or a natural body orifice to observe internal features of a body. Conventional endoscopes include a light transmission pathway, including a fiber light guide, for transmitting light from an external light source through the endoscope to illuminate the internal features of the body. Recently, endoscopes include an internal light source, instead of the combination of the external light source and the fiber light guide, to directly illuminate the internal features of the body. Conventional endoscopes also include an image retrieval pathway for transmitting images of these internal features back to an eyepiece or external video system for processing and display on an external monitor.

During minimally invasive medical procedures, endoscopy provides physicians with visualization of the internal features of the body for accurate diagnosis and/or treatment. For example, rigid endoscopy is utilized in common surgical procedures, such as appendectomy, duodenal ulcer perforation repair, hernia repair, colectomy, splenectomy, adrenalectomy, ovarian cyst removal, ectopic pregnancy, hysterectomy, and so on.

Endoscopes are typically reusable medical devices that must be cleaned and disinfected prior to subsequent uses. A common clinical practice is to clean and disinfect endoscopes between different patients by using, for example, high temperature and/or high pressure processes, such as ethylene oxide sterilization, low temperature plasma disinfection, among other methods. As the endoscope cleaning and disinfection process is cumbersome and the cost of the endoscopic equipment is high, the cleaning and disinfection process can also be expensive. Also, while the endoscope is being processed for re-use, the endoscope is not available for use; thus, affecting a hospital's operational continuity.

Disposable jackets or sheaths may be used to protect endoscopes from contamination during use. Lighting quality and optical imaging quality, however, may drop with the introduction of the disposable jacket over the lighting and imaging pathways of the endoscope. For example, gaps between the distal ends of the endoscope and the disposable jacket and/or light reflected off the disposable jacket may produce stray light which can compromise image quality. It would be desirable to cover and protect an endoscope with a disposable sheath that will not reduce the lighting quality and the imaging quality of the endoscope.

SUMMARY

In accordance with an aspect of the present disclosure, a sheath for covering an endoscope includes a latch assembly, an elongate body extending distally from the latch assembly, and a sheath tip extending distally from the elongate body. The latch assembly includes a main housing and a guide housing, the guide housing movable relative to the main housing to increase a longitudinal length of the latch assembly. The sheath tip has a front face including first and second windows disposed within respective first and second openings defined in the front face. The first and second windows are configured to correspond with respective lighting and imaging windows of an endoscope.

The latch assembly may include a locking mechanism configured to engage a complementary locking structure of an endoscope. In some aspects, the locking mechanism includes opposed keyed locking slots defined in an outer surface of the main housing.

The latch assembly may include an alignment mechanism configured to engage a complementary alignment structure of an endoscope. In some aspects, the alignment mechanism includes an alignment post extending outwardly from an outer surface of the guide housing and proximally into the main housing.

The main housing and the guide housing of the latch assembly may be coaxially aligned with each other and interconnected by elastic members.

The guide housing of the latch assembly may include a proximal portion disposed within the main housing of the latch assembly, with the guide housing extending distally from the main housing and coupled to the elongate body such that a lumen of the elongate body is axially aligned with a through hole of the guide housing.

In accordance with another aspect of the present disclosure, a sheath assembly includes a sheath and a protective sleeve. The sheath includes a latch assembly, an elongate body extending distally from the latch assembly, and a sheath tip extending distally from the elongate body. The latch assembly includes a main housing and a guide housing, the guide housing movable relative to the main housing to increase a longitudinal length of the latch assembly. The sheath tip has a front face including first and second windows disposed within respective first and second openings defined in the front face. The first and second windows are configured to correspond with respective lighting and imaging windows of an endoscope. The protective sleeve is securable to the latch assembly of the sheath.

The guide housing of the latch assembly may include an annular groove defined in an outer surface thereof, the annular groove configured to receive a portion of the protective sleeve therein. In some aspects, the sheath assembly further includes a clamping ring positionable over the annular groove of the guide housing to secure the protective sleeve to the sheath. In certain aspects, the guide housing of the latch assembly includes clips extending outwardly from the guide housing, and the clamping ring includes an annular slot configured to engage the clips and retain the clamping ring on the guide housing.

In accordance with yet another aspect of the present disclosure, a system for covering an endoscope system with a sheath assembly includes an endoscope system and a sheath assembly. The endoscope system includes an endoscope including a handle, a shaft extending distally from the handle, and an endoscope tip disposed at a distal end of the shaft. The endoscope tip has a distal surface including a lighting window and an imaging window. The sheath assembly includes a sheath including a latch assembly, an elongate body extending distally from the latch assembly and configured to receive the shaft of the endoscope therein, and a sheath tip extending distally from the elongate body. The latch assembly includes a main housing and a guide housing, the guide housing movable relative to the main housing to increase a longitudinal length of the latch assembly. The sheath tip has a front face including first and second windows disposed within respective first and second openings defined in the front face. The sheath tip is configured to receive the endoscope tip therein such that the first and second windows are coincident with the lighting and imaging windows of the endoscope.

The endoscope may include a retaining bracket disposed at a distal end of the handle and positioned over the shaft. The retaining bracket may include a locking structure, and the latch assembly of the sheath may include a locking mechanism configured to engage the locking structure of the endoscope to lock the sheath onto the endoscope. In some aspects, the locking mechanism includes opposed keyed locking slots defined in an outer surface of the main housing of the latch assembly, and the locking structure includes opposed keyed locking protrusions disposed on an inner surface of an outer collar of the retaining bracket.

The retaining bracket of the endoscope may include an alignment structure, and the latch assembly of the sheath may include an alignment mechanism configured to engage the alignment structure of the endoscope to align the first and second windows of the sheath tip with the lighting and imaging windows of the endoscope tip. In some aspects, the alignment mechanism includes an alignment post extending outwardly from an outer surface of the guide housing and proximally into the main housing of the latch assembly, and the alignment structure includes an alignment slot defined in an outer surface of an inner collar of the retaining bracket.

The elongate body of the sheath may be shorter in length than the shaft of endoscope, and the latch assembly of the sheath may include elastic members interconnecting the main housing and the guide housing such that the guide housing is movable relative to the main housing to increase the length of the elongate body of the sheath when the shaft of the endoscope is placed therein to ensure that the front face of the sheath tip contacts the distal surface of the endoscope tip.

The endoscope system may further include a system control box and a cable interconnecting the endoscope with the system control box, and the sheath assembly may further include a protective sleeve securable to the latch assembly of the sheath and positionable over the handle of the endoscope and the cable of the endoscope system. In some aspects, a portion of the protective sleeve is positionable and securable within an annular groove defined in an outer surface of the guide housing of the latch assembly. In certain aspects, the sheath assembly further includes a clamping ring positionable over the annular groove of the guide housing to secure the protective sleeve to the sheath.

Embodiments of the present disclosure can include one or more of the following advantages.

In embodiments, the sheaths and sheath assemblies are consumable (e.g., one time use) items that protect an endoscope and/or endoscope system to eliminate or reduce the need for cleaning and disinfection procedures requiring high temperature and/or high pressure. The sheath/sheath assemblies can cover and protect surfaces of the endoscope and/or the endoscope system that may be exposed to contamination. In some embodiments, the sheath assemblies include a protective sleeve securable to the sheath in sealing relationship therewith to isolate and protect the entirety of the endoscope as well as the cable which extends from the endoscope. Thus, the sheaths and sheath assemblies can reduce the down time of the endoscope, reduce the exposure of the endoscope to the harsh environments associated with high temperature and high pressure cleaning and disinfection procedures, and keep costs down.

In embodiments, the sheath includes structures that mechanically match structures of the endoscope, e.g., the optical and lighting devices, to minimize optical quality drop as compared to conventional sheaths.

In some embodiments, the sheath has a front face including two windows that are isolated from each other and configured to correspond with the lighting and imaging pathways of an endoscope thereby eliminating or reducing the introduction of stray light into the endoscope and maintaining lighting quality and imaging quality comparable to an endoscope without an endoscope sheath disposed thereover. Additionally or alternatively, the latch assembly includes an alignment feature to ensure that the two windows are properly aligned with the lighting and imaging pathways.

In some embodiments, the length of the elongate body of the sheath is shorter than the length of the shaft of the endoscope, and elastic members disposed within the latch assembly of the sheath longitudinally expand the latch assembly when the sheath is placed on the endoscope to ensure the front face of the sheath is disposed immediately adjacent the front face of the endoscope. This contacting arrangement eliminates or reduces the introduction of stray light into the endoscope and maintains the light quality and imaging quality of the endoscope.

In embodiments, the sheath locks onto an endoscope about the rear or proximal portion thereof (e.g., adjacent the handle of the endoscope), making installation of the sheath on the endoscope easier as compared to sheaths that connect about a front or distal portion thereof or sheaths that do not have a locking mechanism.

Other aspects, features, and advantages will be apparent from the description, the drawings, and the claims.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Figure 2:
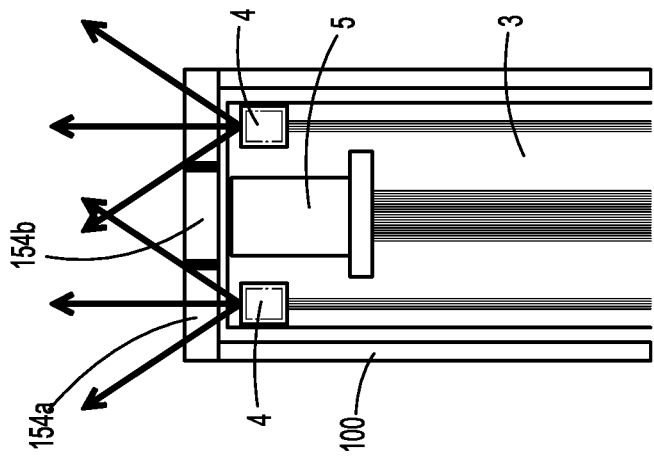
FIG. 2 is a schematic illustration of a tip section of a sheath in accordance with an embodiment of the present disclosure, positioned over a front-end section of an endoscope.

Embodiments of the present disclosure are now described in detail with reference to the drawings in which like reference numerals designate identical or corresponding elements in each of the several views. Throughout this description, the term "proximal" refers to a portion of a system, a device, or a component thereof, that is closer to a user, and the term "distal" refers to a portion of the system, the device, or the component thereof, that is farther from the user.

Figure 1:
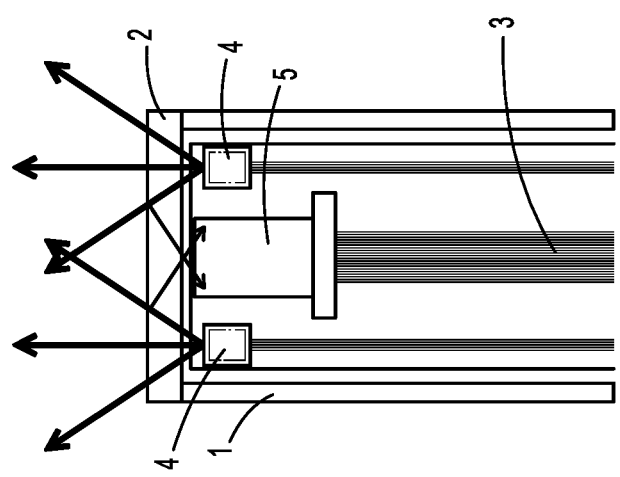
FIG. 1 is a schematic illustration of a tip section of a sheath in accordance with the prior art, positioned over a front-end section of an endoscope.

Referring initially to FIG. 1, a prior art sheath 1 having a front-end illumination window 2 is shown disposed on an endoscope 3 having a front or forward facing lighting system including a light source 4, such as light emitting diodes (LEDs), disposed radially outward of a lens 5. For lighting systems having a relatively large divergence angle of the lighting pathway, such as LED lighting systems, the light emitted from the light source 4 is reflected back from the inner and outer surfaces of the illumination window 2 of the sheath 1 and into the imaging pathway of the lens 5. This phenomenon causes stray light that affects image quality.

As shown in FIG. 2, a sheath 100 in accordance with an embodiment of the present disclosure includes a front-end having two separate windows 154a, 154b corresponding to the lighting pathway and the imaging pathway, respectively, of the endoscope 3. The windows 154a, 154b are isolated from each other, and positioned immediate adjacent (e.g., in contact with) the distal end of the endoscope 3, thereby preventing or minimizing any reflected light from entering the imaging pathway.

Figure 3:
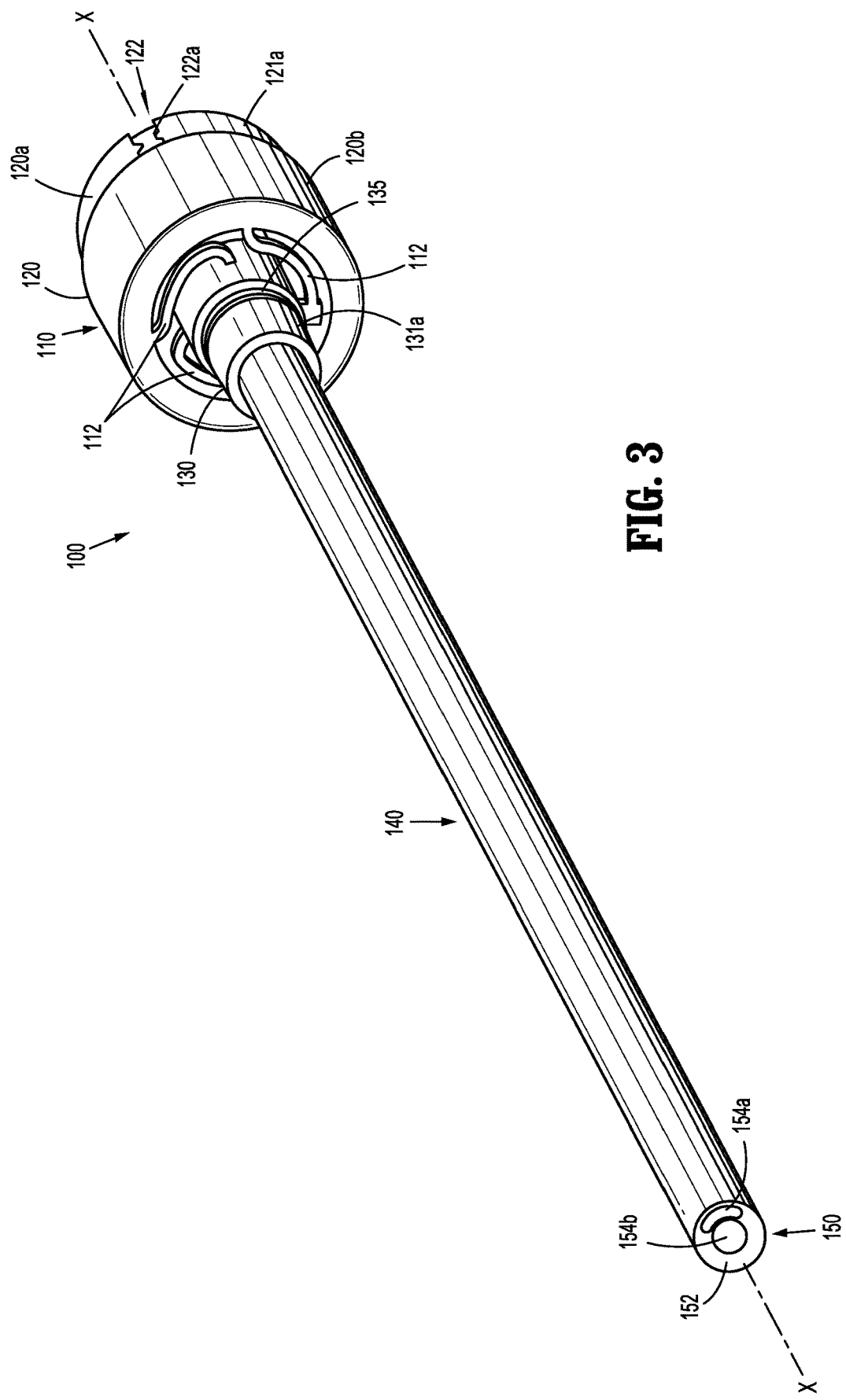
FIG. 3 is a perspective view of a sheath in accordance with an embodiment of the present disclosure.
Figure 4:
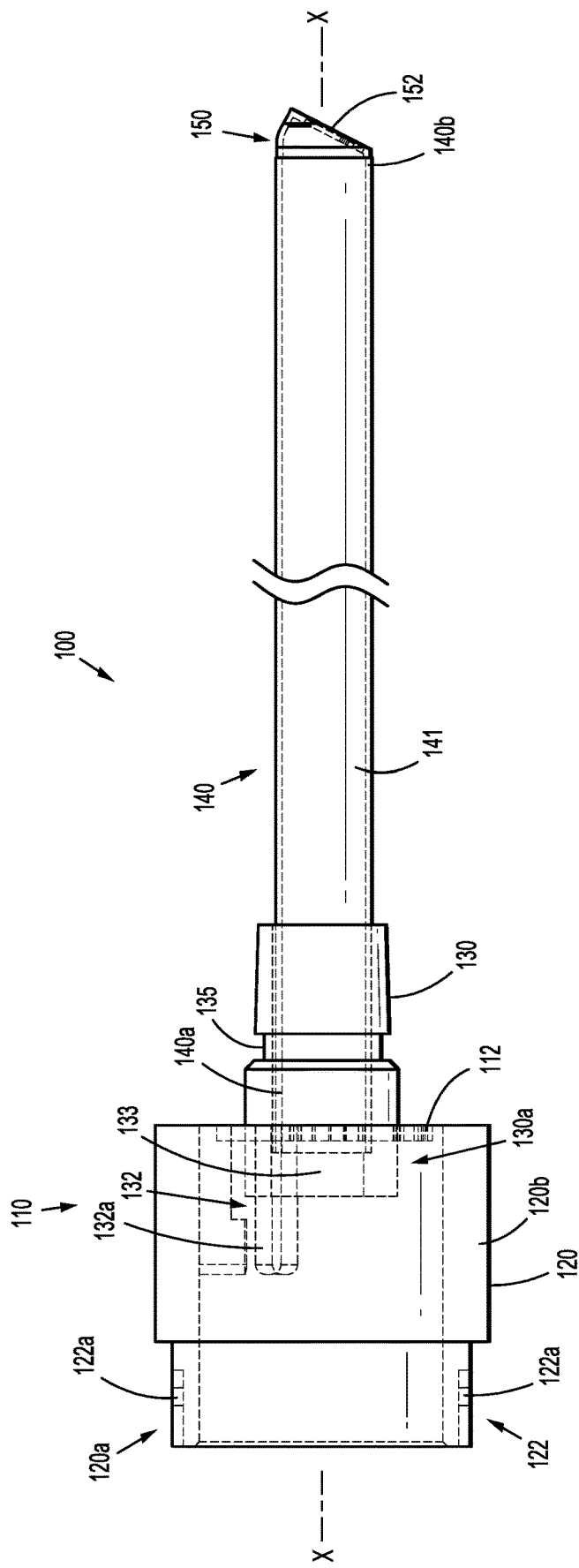
FIG. 4 is a side view, in partial cross-section, of the sheath of FIG. 3.
Figure 6:
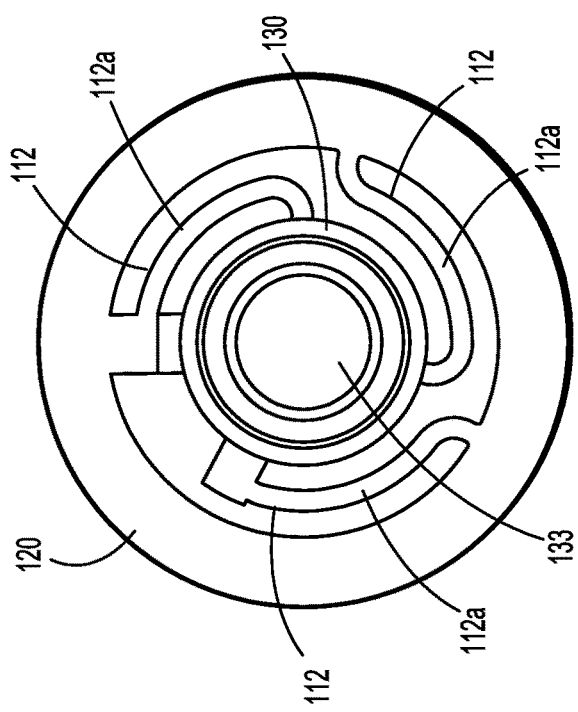
FIG. 6 is an end view of a distal end of the latch assembly of the sheath of FIGS. 3 and 4.

Turning now to FIGS. 3 and 4, the sheath 100 extends along a longitudinal axis "X", and includes a latch assembly 110 having a main housing 120 and a guide housing 130, an elongate body 140 extending distally from the latch assembly 110, and a sheath tip 150 extending distally from the elongate body 140. The sheath 100 is configured for positioning over an endoscope to isolate the endoscope from the external environment.

Figure 5:
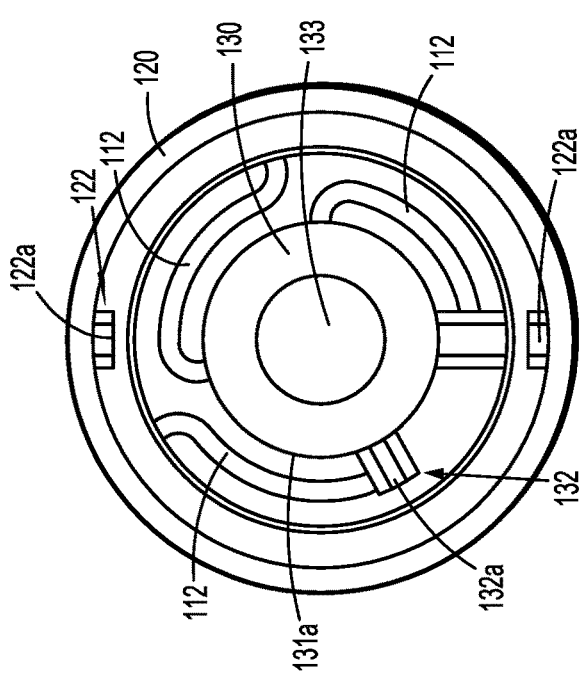
FIG. 5 is an end view of a proximal end of a latch assembly of the sheath of FIGS. 3 and 4.

As shown in FIGS. 3-5, the main housing 120 of the latch assembly 110 includes a proximal portion 120a having a locking mechanism 122 configured to engage a complementary locking structure of an endoscope. In embodiments, the locking mechanism 122 includes opposed keyed locking slots 122a defined in an outer surface 121a of the proximal portion 120a of the main housing 120. The main housing 120 also a grip portion 120b configured for engagement (e.g., holding/handling) by a user.

The guide housing 130 includes a proximal portion 130a disposed within the main housing 120 of the latch assembly 110. The proximal portion 130a of the guide housing 130 includes an alignment mechanism 132 configured to engage a complementary alignment structure of an endoscope. In embodiments, the alignment mechanism 132 includes an alignment post 132a extending radially outward from an outer surface 131a of the proximal portion 130a of the guide housing 130, and proximally therefrom within the main housing 120.

As shown in FIGS. 3-6, the main housing 120 and the guide housing 130 are coaxially aligned with each other and interconnected by elastic members 112. Each elastic member 112 is coupled, either directly or indirectly, to both the main and guide housings 120, 130 such that a central portion 112a of the elastic member 112 extends radially between the main and guide housings 120, 130 (e.g., coaxially aligned with the main and guide housings) in spaced relation relative to each other.

The elastic members 112 are flexible, e.g., elasticized, stretchable, or yieldable, to allow the guide housing 130 to move longitudinally relative to the main housing 120 from a biased, first position to an elongated, second position to increase the longitudinal length of the latch assembly 110, and thus the sheath 100. The elastic members 112 may be in the form of bands, tethers, ropes, cords, cables, straps, etc., and may formed from, for example, an elastomer, silicone, rubber, latex, among other resilient materials within the purview of those skilled in the art.

The guide housing 130 extends distally from main housing 120 and defines a through-hole 133 extending longitudinally therethrough that acts as a guide hole for guiding the insertion of an endoscope therethrough. An annular groove 135 is defined in the outer surface 131a of the guide housing 130 and configured for attachment of a protective sleeve thereto, as described in further detail below.

With reference again to FIGS. 3 and 4, the elongate body 140 is a rigid tubular member having a uniform diameter along the length thereof, and defines a lumen 141 therethrough. The elongate body 140 has a proximal end 140a disposed in sealing relation within the guide housing 130 of the latch assembly 110 such that the lumen 141 is axially aligned with the through hole 133 of the guide housing 130 along the longitudinal axis "X" of the sheath 100. The elongate body 140 also has a distal end 140b integrally formed with, or secured to, the sheath tip 150.

Figure 7:
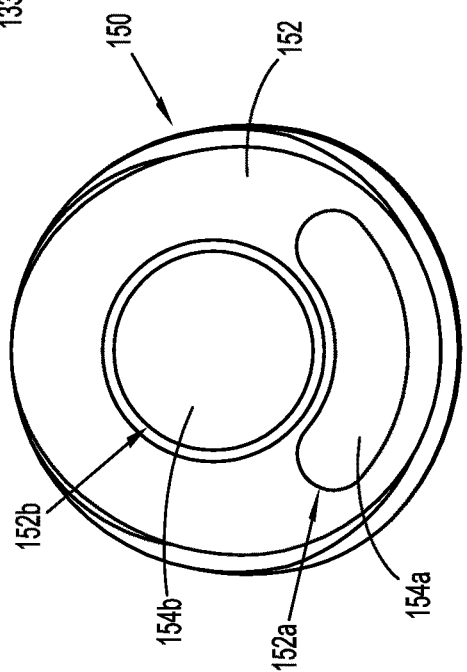
FIG. 7 is an end view of a sheath tip of the sheath of FIGS. 3 and 4.

The sheath tip 150 is sized and shaped to correspond with the configuration of an endoscope tip. As shown in FIG. 7, in conjunction with FIGS. 3 and 4, the sheath tip 150 has a front face or distal end 152 including first and second windows 154a, 154b sealingly positioned within first and second openings 152a, 152b, respectively, defined in the distal end 152 of the sheath tip 150. The first and second openings 152a, 152b of the distal end 152 of the sheath tip 150 are separate and distinct, having defined peripheral boundaries. The first and second windows 154a, 154b may be formed from glass, polymers, among other transparent materials within the purview of those skilled in the art. The first and second openings 152a, 152b and thus, the first and second windows 154a, 154b are sized, shaped, and positioned within the distal end 152 of the sheath tip 150 in a configuration that corresponds with the lighting and imaging pathways of an endoscope.

Figure 8:
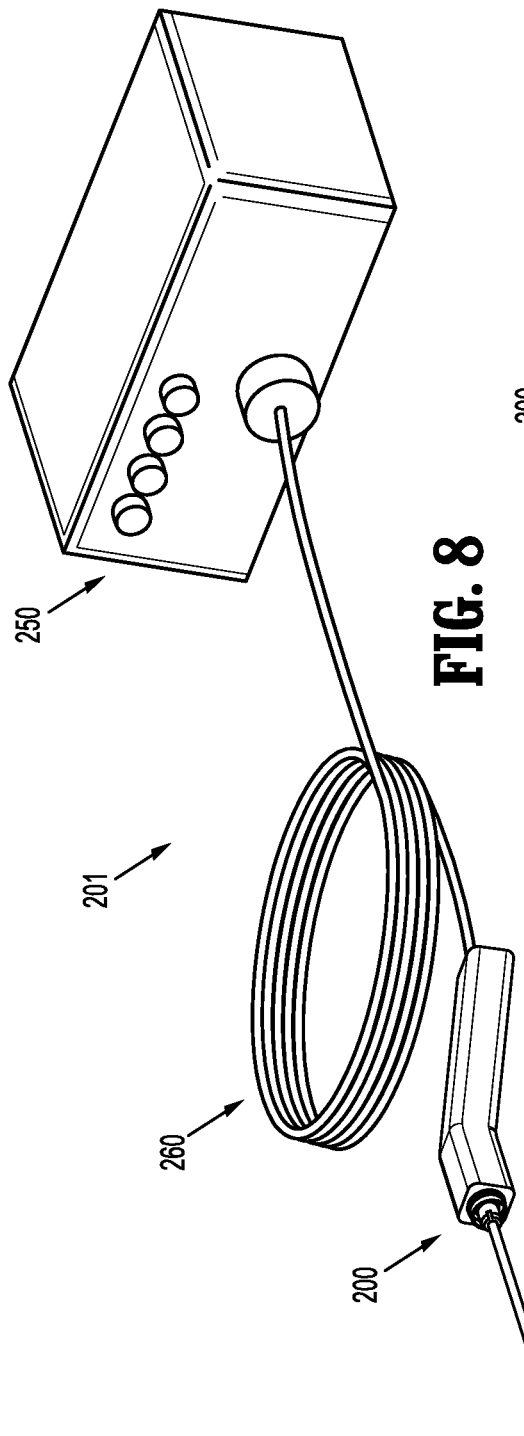
FIG. 8 is a perspective view of an endoscope system in accordance with an embodiment of the present disclosure.

With reference now to FIG. 8, an endoscope system 201 in accordance with an embodiment of the present disclosure is shown. The endoscope system 201 includes an endoscope 200, a system control box 250, and a power cord or cable 260 interconnecting the endoscope 200 with the system control box 250. The system control box 250 includes software and hardware components for powering and/or controlling a camera and/or a light source of the endoscope 200, and/or for processing images captured by the camera and outputting video signals to a display (not shown) to display the captured images. The cable 260 is a transmission line between the endoscope 200 and the system control box 250, and may be long in length (e.g., 3 meters or more).

Figure 9:
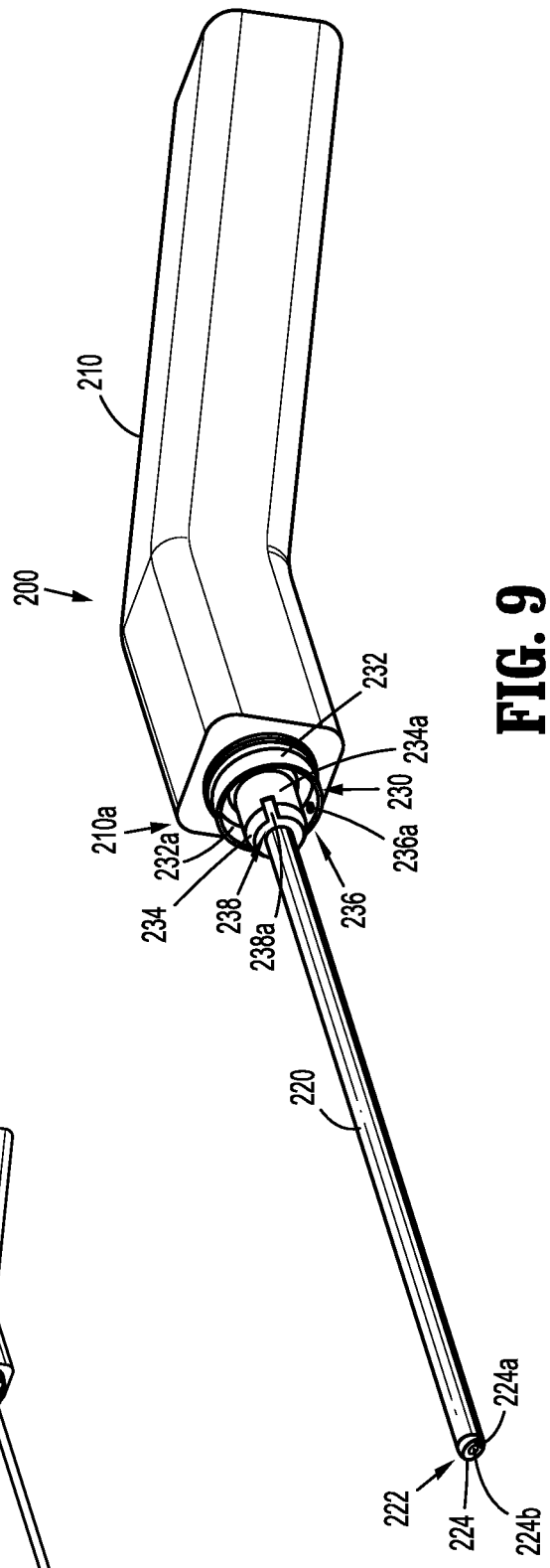
FIG. 9 is a perspective view of an endoscope of the endoscope system of FIG. 8.

As shown in FIG. 9, the endoscope 200 includes a handle 210 and a shaft or insertion tube 220 extending distally from the handle 210 that terminates at an endoscope tip 222. The handle 210 is used by a user to control and manipulate the endoscope 200. A retaining bracket 230 is disposed at a distal end 210a of the handle 210, and is positioned over the shaft 220. The retaining bracket 230 includes an outer collar 232, and an inner collar 234 disposed within the outer collar 232 in spaced relation relative thereto. Alternatively, the inner collar 234 may be separate from the retaining bracket 230.

The outer collar 232 has a locking structure 236 disposed on an inner surface 232a thereof, and the inner collar 234 has an alignment structure 238 disposed on an outer surface 234a thereof. In embodiments, the locking structure 236 includes keyed locking protrusions 236a that are configured to mate with the locking slots 122a of the latch assembly 110 of the sheath 100, and/or the alignment structure 238 is an alignment slot 238a that is configured to receive the alignment post 132a of the latch assembly 110 therein.

The endoscope tip 222 includes a lighting device and an imaging device (not explicitly shown) disposed therein, and a distal surface 224 including a first or lighting window 224a and a second or imaging window 224b disposed over the respective lighting and imaging devices to provide lighting and imaging pathways of the endoscope 200. The size and shape of the endoscope tip 222 corresponds to the size and shape of the sheath tip 150 (see e.g., FIG. 3), and the boundaries of the lighting and imaging windows 224a, 224b are coincident with the boundaries of the first and second windows 154a, 154b (see e.g., FIG. 7) of the sheath tip 150.

With continued reference to FIG. 9, in conjunction with FIG. 4, the sheath 100 is placed over the endoscope 200 by inserting the endoscope tip 222 into the proximal portion 120a of the main housing 120 of the latch assembly 110, and passing the endoscope tip 222 proximally through the through hole 133 of the guide housing 130 and the lumen 141 of the elongate body 140 until the endoscope tip 222 is disposed within the sheath tip 150. During movement of the endoscope 200 through the sheath 100, the alignment post 132a slides into, and engages, the alignment slot 238a of the endoscope 200 to ensure that the sheath tip 150 is properly oriented relative to the endoscope tip 222. Accordingly, the sheath 100 and/or the endoscope 200 may need to be rotated relative to the other to align and unite the alignment mechanism 132 with the alignment structure 238.

The endoscope 200 is passed through the sheath 100 until the latch assembly 110 of the sheath 100 engages the retaining bracket 230 of the endoscope 200. Specifically, the proximal portion 120a of the main housing 120 of the latch assembly 110 enters the space defined between the outer and inner collars 232, 234 of the retaining bracket 230, and the locking slots 122a receive the locking protrusions 236a of the endoscope 200 to lock the sheath 100 on the endoscope 200.

The length of the elongate body 140 of the sheath 100 is shorter than the length of the shaft 220 of the endoscope 200. Accordingly, during placement of the sheath 100 on the endoscope 200, the elastic members 112 disposed within the latch assembly 110 flex or stretch a longitudinal distance to accommodate for the length difference between the elongate body 140 and the shaft 220, and to ensure that the distal end 152 of the sheath tip 150 is positioned immediate adjacent to, and contacts, the distal surface 224 of the endoscope tip 222 (e.g., no gaps are formed therebetween).

The direction fitting of the sheath tip 150 relative to the endoscope tip 220 via engagement of the alignment mechanism 132 of the sheath 100 and the alignment structure 238 of the endoscope 200, the matching configuration of the first and second windows 154a, 154b of the sheath tip 150 and the lighting and imaging windows 224a, 224b of the endoscope tip 220, and the tight fit between the sheath tip 150 and the endoscope tip 220 eliminate or reduce stray light which may be introduced into the endoscope 200 from the sheath 100 such that optical performance of the endoscope 200 is minimally affected by the use of the sheath 100.

Figure 10:
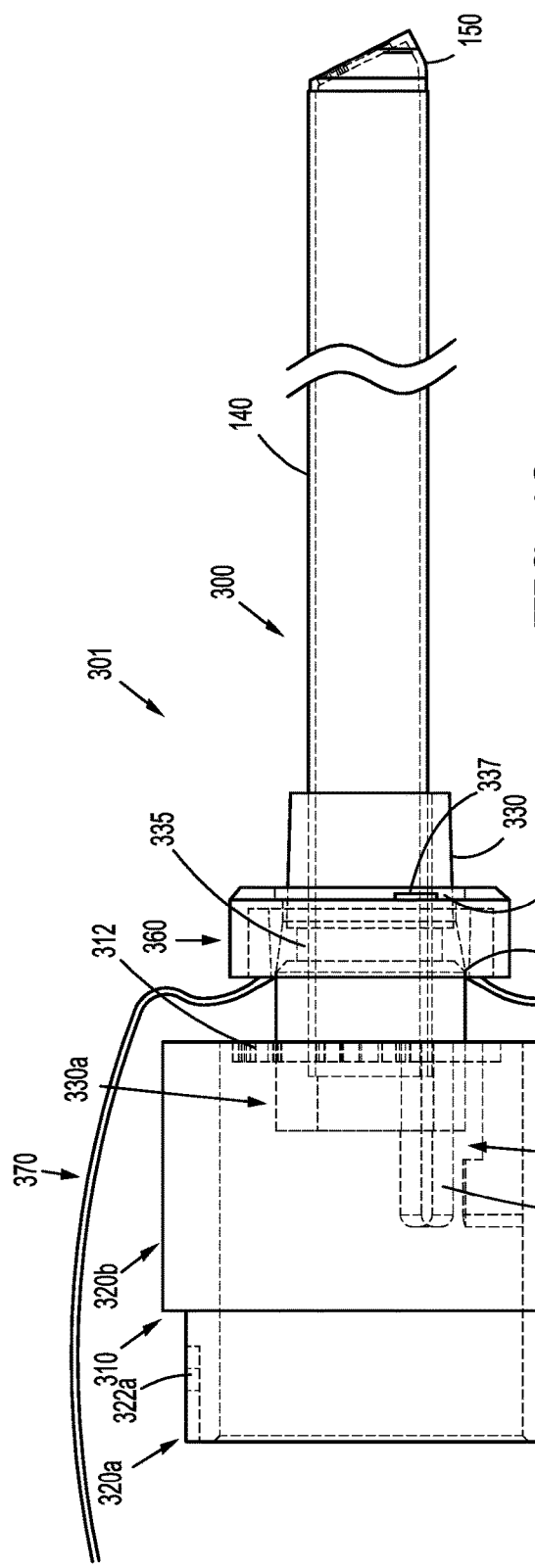
FIG. 10 is a side view, in partial cross-section, of a sheath assembly in accordance with an embodiment of the present disclosure.

With reference now to FIG. 10, a sheath assembly 301 in accordance with an embodiment of the present disclosure is shown. The sheath assembly 301 includes a sheath 300, a retaining or clamping ring 360, and a protective sleeve 370. The sheath 300 is substantially similar to the sheath 100 and therefore described with respect to the differences therebetween. The sheath 300 includes a latch assembly 310 having a main housing 320 and a guide housing 330, an elongate body 140 extending distally from the latch assembly 310, and a sheath tip 150 extending distally from the elongate body 140.

Figure 11:
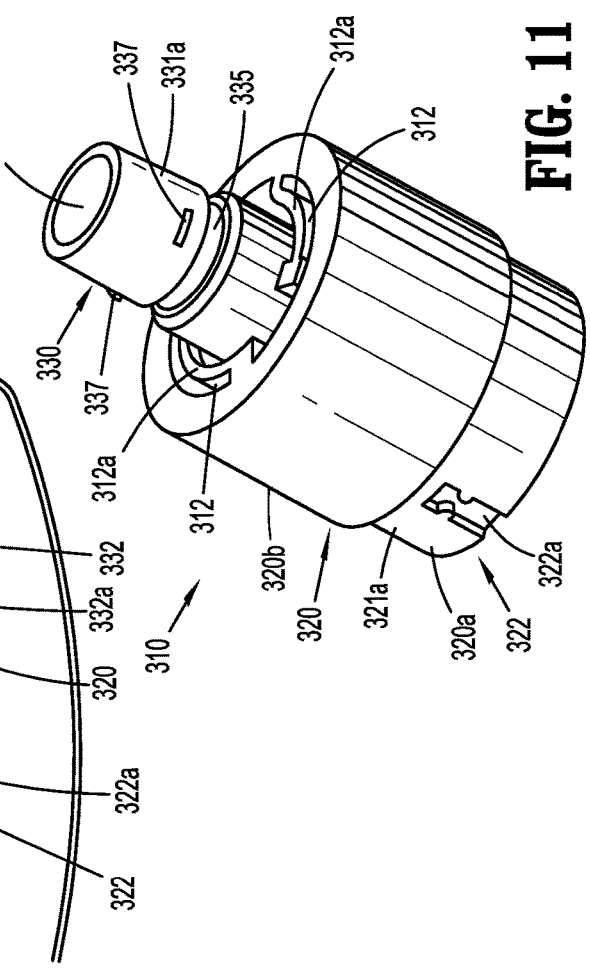
FIG. 11 is a perspective view of a latch assembly of a sheath of the sheath assembly of FIG. 10.

As shown in FIGS. 10 and 11, the main housing 320 of the latch assembly 310 includes a proximal portion 320a having a locking mechanism 322 configured to engage a complementary locking structure of an endoscope. In embodiments, the locking mechanism 322 includes opposed keyed locking slots 322a defined in an outer surface 321a of the proximal portion 320a of the main housing 320. The main housing 320 also a grip portion 320b configured for engagement (e.g., holding/handling) by a user.

The guide housing 330 includes a proximal portion 330a disposed within the main housing 320 of the latch assembly 310. The proximal portion 330a of the guide housing 330 includes an alignment mechanism 332 configured to engage a complementary alignment structure of an endoscope. In embodiments, the alignment mechanism 332 includes an alignment post 332a extending radially outward from an outer surface 331a of the proximal portion 330a of the guide housing 330, and proximally therefrom within the main housing 320.

The main housing 320 and the guide housing 330 are coaxially aligned with each other and interconnected by elastic members 312. Each elastic member 312 is coupled, either directly or indirectly, to both the main and guide housings 320, 330 such that a central portion 312a of the elastic member 312 extends radially between the main and guide housings 320, 330 (e.g., coaxially aligned with the main and guide housings) in spaced relation relative to each other.

The guide housing 330 extends distally from main housing 320 and defines a through-hole 333 extending longitudinally therethrough that acts as a guide hole for guiding the insertion of an endoscope therethrough. An annular groove 335 is defined in the outer surface 331a of the guide housing 330 and configured for attachment of the protective sleeve 370 thereto. Clips 337 are disposed around the outer surface 331a of the guide housing 330 in spaced relation relative to each other, and distal to the annular groove 335. The clips 337 project radially outward from the guide housing 330 and are configured to engage the clamping ring 360. The clips 337 may be ridges, protrusions, bumps, among other projections that are configured to engage a mating structure of the clamping ring 360.

Figure 12:
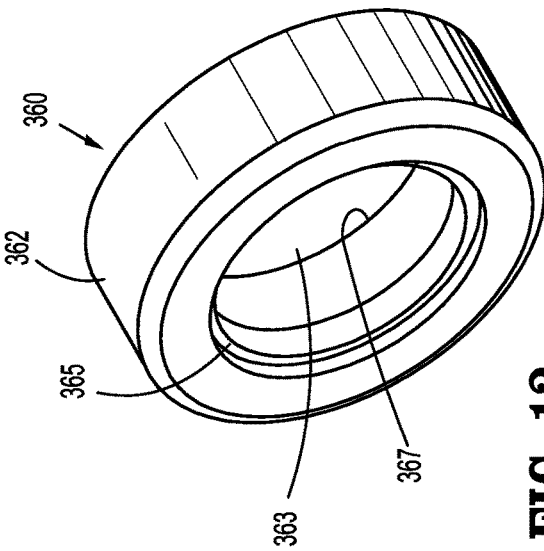
FIG. 12 is a perspective view of a clamping ring of the sheath assembly of FIG. 10.

As shown in FIGS. 10 and 12, the clamping ring 360 includes an annular body 362 having a central opening 363 defined therethrough, an annular slot 365 defined therein, and a clamping edge 367. The clamping ring 360 is positionable on the guide housing 330 of the latch assembly 310 such that the clips 337 of the guide housing 330 engage the annular slot 365 of the clamping ring 360 to retain the clamping ring 360 on the guide housing 330.

The protective sleeve 370 is a sterile cover or drape of sufficient size and length to cover and enclose the endoscope and the cable of an endoscope system. The protective sleeve 370 is formed from a flexible, thin film or web of material that is sufficiently strong to allow for attachment of the protective sleeve 370 to the sheath 100 and manipulation of controls which may be disposed on the handle of an endoscope, without tearing, yet is flexible to allow for movement of the protective sleeve 370 during movement of the endoscope. The protective sleeve 370 is also impervious or impermeable to contaminants to maintain a sterile boundary between the covered components of an endoscope system and the external environment. The protective sleeve 370 may be transparent for an unobscured view of the endoscope and/or cable disposed therein. The protective sleeve 370 may be formed from polymers, such as plastic, among other suitable materials that may be formed into films.

Figure 13:
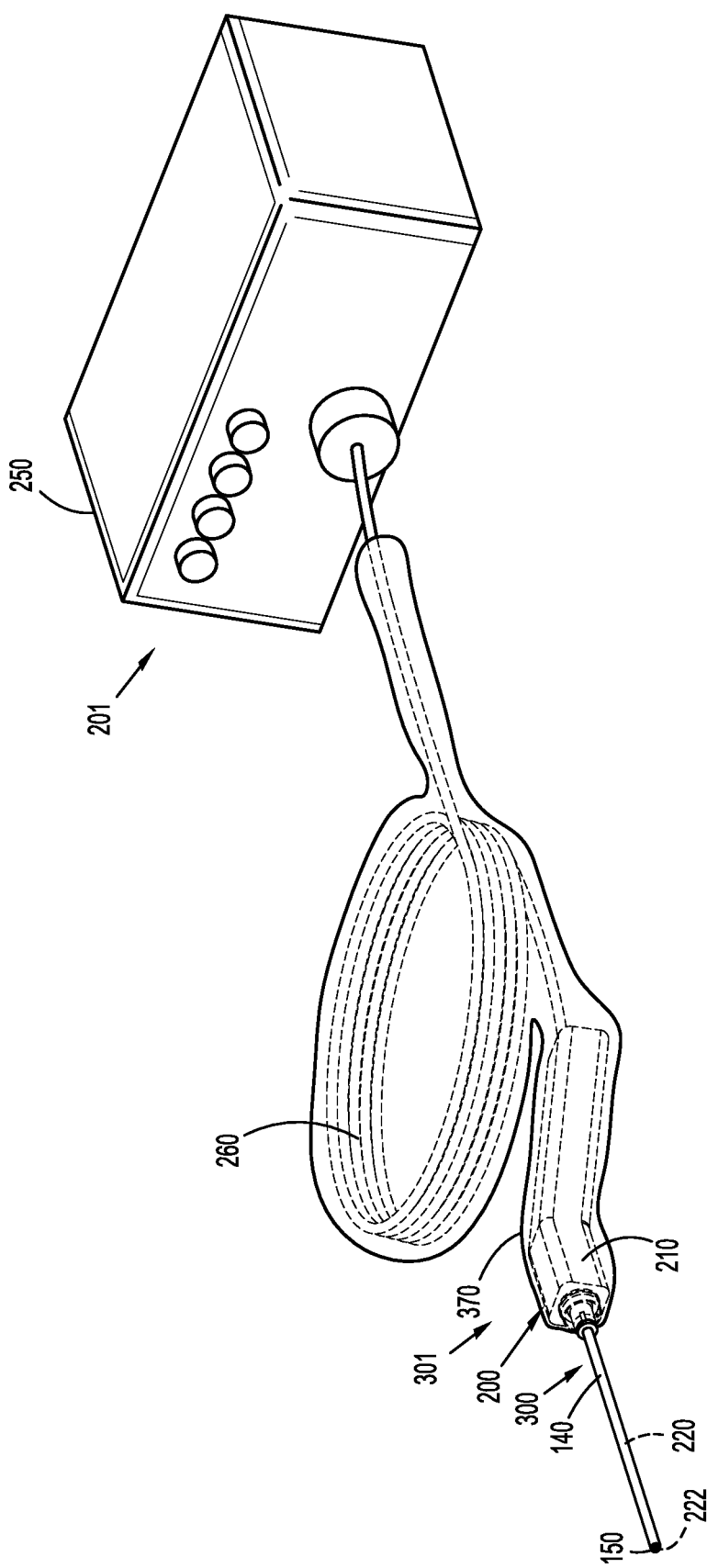
FIG. 13 is a perspective view of the endoscope system of FIG. 8 and the sheath assembly of FIG. 10.

Turning now to FIG. 13, the sheath assembly 301 is utilized with the endoscope system 201 for isolating components (e.g., the endoscope 200 and the cable 260) of the endoscope system 201 from the external environment to prevent or minimize contamination of the endoscope system 201 during use in a surgical procedure. The sheath 300 is installed on the endoscope 200 in a similar manner as described above with respect to the sheath 100.

With continued reference to FIG. 13, in conjunction with FIGS. 9 and 10, the sheath 300 is placed over the endoscope 200 by inserting the endoscope tip 222 into the proximal portion 320a of the main housing 320 of the latch assembly 310 and sliding the sheath 300 over the endoscope 200 until the locking mechanism 322 of the sheath 300 engages the locking structure 236 of the endoscope 200. During movement of the endoscope 200 through the sheath 300, the alignment mechanism 332 engages the alignment structure 238 of the endoscope 200 to ensure that the sheath tip 150 is properly oriented relative to the endoscope tip 222, and the elastic members 312 of the latch assembly 310 stretch to accommodate for the length difference between the elongate body 140 of the sheath 100 and the shaft 220 of the endoscope 200 to ensure that the sheath tip 150 contacts the endoscope tip 222.

The protective sleeve 370 is positioned over the cable 260 and the handle 210 of the endoscope 200, with a portion of the protective sleeve 370 positioned in the annular groove 335 of the guide housing 330 of the latch assembly 310 of the sheath 300. The clamping ring 360 is then placed over the portion of the protective sleeve 370 disposed within the annular groove 335 by sliding the clamping ring 360 in a proximal direction over the sheath tip 150, the elongate body 140, and the guide housing 330 until the clamping edge 367 engages the guide housing 330, capturing the protective sleeve 370 therebetween, and the annular slot 365 engages the clips 337 to retain the clamping ring 360 and thus, the protective sleeve 370, to the latch assembly 310. Accordingly, the endoscope 200 and the cable 260, each of which is conventionally sterilized after use, are protected by the sheath assembly 301.

While the endoscope system 201 has been described as being protected by the sheath assembly 301, it should be appreciated that the endoscope sheath 100 may be utilized with a protective sleeve 370 to cover the endoscope system 201. In such embodiments, the protective sleeve 370 is positioned over the handle 210 of the endoscope 200 and the cable 260, as discussed above, with a portion of the protective sleeve 370 disposed within, and secured to, the annular groove 135 of the guide housing 130 (e.g., via a band, cord, rope, tether, etc.).

Further, as another example, it should be understood that the locking mechanism 122, 322 of the sheath 100, 300 and the locking structure 236 of the endoscope 200 may additionally or alternatively include other suitable mechanical arrangements that form a connect/disconnect interface for releasably securing the sheath 100, 300 to the endoscope 200. Similarly, the alignment mechanism 132, 332 of the sheath 100, 300 and the alignment structure 238 of the endoscope 200 may have other suitable mechanical arrangements that maintain the unique clocking position of the sheath 100, 300 over the endoscope 200 for mistake-proofing the installation of the sheath 100, 300 on the endoscope 200.

As yet another example, while the sheath tip 150 has been described and shown as having a beveled distal end 152 including the first and second windows 154a, 154b, it should be appreciated that the sheath tip 150 may have any shape that corresponds with the shape of an endoscope tip, and the configuration and number of windows of the sheath tip 150 may vary to match that of an endoscope tip.

As another example, the retaining bracket 230 of the endoscope 200 may be an adapter made for installation on an endoscope such that any endoscope (e.g., rigid endoscopes and/or endoscopes having LED front lighting systems) may be fitted with an endoscope sheath 100, 300 or sheath assembly 301 of the present disclosure.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described. Thus, other embodiments are within the scope of the following claims.

What is claimed is:

1. A sheath for covering an endoscope, comprising:
a latch assembly including a main housing, a guide housing coaxially aligned with the main housing, and elastic members interconnecting the main housing and the guide housing, each of the elastic members including a first end coupled to the main housing and a second end coupled to the guide housing, the first and second ends radially offset with respect to each other, the elastic members longitudinally stretchable to allow the guide housing to move relative to the main housing from a biased, first position to an elongated, second position to increase a longitudinal length of the latch assembly;
an elongate body extending distally from the latch assembly; and a sheath tip extending distally from the elongate body, the sheath tip having a front face including first and second windows disposed within respective first and second openings defined in the front face, the first and second windows configured to correspond with respective lighting and imaging windows of an endoscope.

2. The sheath according to claim 1, wherein the latch assembly includes a locking mechanism configured to engage a complementary locking structure of an endoscope.

3. The sheath according to claim 2, wherein the locking mechanism includes opposed keyed locking slots defined in an outer surface of the main housing.

4. The sheath according to claim 1, wherein the latch assembly includes an alignment mechanism configured to engage a complementary alignment structure of an endoscope.

5. The sheath according to claim 4, wherein the alignment mechanism includes an alignment post extending outwardly from an outer surface of the guide housing and proximally into the main housing.

6. The sheath according to claim 1, wherein the guide housing includes a proximal portion disposed within the main housing of the latch assembly, the guide housing extending distally from the main housing and coupled to the elongate body such that a lumen of the elongate body is axially aligned with a through hole of the guide housing.

7. A sheath assembly comprising:
the sheath according to claim 1; and
a protective sleeve securable to the latch assembly of the sheath.

8. The sheath assembly according to claim 7, wherein the guide housing of the latch assembly includes an annular groove defined in an outer surface thereof, the annular groove configured to receive a portion of the protective sleeve therein.

9. The sheath assembly according to claim 8, further comprising a clamping ring positionable over the annular groove of the guide housing to secure the protective sleeve to the sheath.

10. The sheath assembly according to claim 9, wherein the guide housing of the latch assembly includes clips extending outwardly from the guide housing, and the clamping ring includes an annular slot configured to engage the clips and retain the clamping ring on the guide housing.

11. A system for covering an endoscope system with a sheath assembly, comprising:
an endoscope system comprising:
an endoscope including a handle, a shaft extending distally from the handle, and an endoscope tip disposed at a distal end of the shaft, the endoscope tip having a distal surface including a lighting window and an imaging window; and
a sheath assembly comprising:
a sheath including:
a latch assembly including a main housing, a guide housing coaxially aligned with the main housing, and elastic members interconnecting the main housing and the guide housing, each of the elastic members including a first end coupled to the main housing and a second end coupled to the guide housing, the first and second ends radially offset with respect to each other, the elastic members longitudinally stretchable to allow the guide housing to move relative to the main housing from a biased, first position to an elongated, second position to increase a longitudinal length of the latch assembly;
an elongate body extending distally from the latch assembly, the elongate body configured to receive the shaft of the endoscope therein; and
a sheath tip extending distally from the elongate body, the sheath tip having a front face including first and second windows disposed within respective first and second openings defined in the front face, the sheath tip configured to receive the endoscope tip therein such that the first and second windows are coincident with the lighting and imaging windows of the endoscope.

12. The system according to claim 11, wherein the endoscope includes a retaining bracket disposed at a distal end of the handle and positioned over the shaft, the retaining bracket including a locking structure, and the latch assembly of the sheath includes a locking mechanism configured to engage the locking structure of the endoscope to lock the sheath onto the endoscope.

13. The system according to claim 12, wherein the locking mechanism includes opposed keyed locking slots defined in an outer surface of the main housing of the latch assembly, and the locking structure includes opposed keyed locking protrusions disposed on an inner surface of an outer collar of the retaining bracket.

14. The system according to claim 12, wherein the retaining bracket of the endoscope includes an alignment structure, and the latch assembly of the sheath includes an alignment mechanism configured to engage the alignment structure of the endoscope to align the first and second windows of the sheath tip with the lighting and imaging windows of the endoscope tip.

15. The system according to claim 14, wherein the alignment mechanism includes an alignment post extending outwardly from an outer surface of the guide housing and proximally into the main housing of the latch assembly, and the alignment structure includes an alignment slot defined in an outer surface of an inner collar of the retaining bracket.

16. The system according to claim 11, wherein the elongate body of the sheath is shorter in length than the shaft of endoscope, and wherein the elastic members stretch a longitudinal distance to accommodate for a length difference between the elongate body and the shaft when the shaft of the endoscope is placed therein to ensure that the front face of the sheath tip contacts the distal surface of the endoscope tip.

17. The system according to claim 11, wherein the endoscope system further comprises a system control box and a cable interconnecting the endoscope with the system control box, and the sheath assembly further comprises a protective sleeve securable to the latch assembly of the sheath and positionable over the handle of the endoscope and the cable of the endoscope system.

18. The system according to claim 17, wherein a portion of the protective sleeve is positionable and securable within an annular groove defined in an outer surface of the guide housing of the latch assembly.

19. The system according to claim 18, wherein the sheath assembly further comprises a clamping ring positionable over the annular groove of the guide housing to secure the protective sleeve to the sheath.

* * * * *